(12) United States Patent
Binder et al.

(10) Patent No.: US 7,824,671 B2
(45) Date of Patent: Nov. 2, 2010

(54) RETINAL PIGMENT EPITHELIAL CELL CULTURES ON AMNIOTIC MEMBRANE AND TRANSPLANTATION

(75) Inventors: Susanne Binder, Vienna (AT); Scheffer C. G. Tseng, Pinecrest, FL (US)

(73) Assignee: Tissuetech, Inc., Miami, FL (US)

(*) Notice: Subject to any disclaimer, the term of this patent is extended or adjusted under 35 U.S.C. 154(b) by 242 days.

(21) Appl. No.: 10/530,164

(22) PCT Filed: Oct. 6, 2003

(86) PCT No.: PCT/US03/31464
§ 371 (c)(1),
(2), (4) Date: Apr. 4, 2005

(87) PCT Pub. No.: WO2004/033635
PCT Pub. Date: Apr. 22, 2004

(65) Prior Publication Data
US 2006/0002900 A1 Jan. 5, 2006

Related U.S. Application Data

(60) Provisional application No. 60/415,986, filed on Oct. 4, 2002.

(51) Int. Cl.
A61K 35/44 (2006.01)
A61K 35/50 (2006.01)
C12N 5/071 (2010.01)

(52) U.S. Cl. ............ 424/93.7; 424/424; 424/427; 424/571; 424/583; 435/371

(58) Field of Classification Search ............. 424/93.7, 424/424, 427, 571, 583; 435/371
See application file for complete search history.

(56) References Cited

U.S. PATENT DOCUMENTS

| | | | | |
|---|---|---|---|---|
| 6,045,791 | A * | 4/2000 | Liu | 424/93.7 |
| 6,152,142 | A * | 11/2000 | Tseng | 128/898 |
| 6,326,019 | B1 | 12/2001 | Tseng | 424/424 |
| 2002/0039788 | A1 | 4/2002 | Isseroff | 435/366 |
| 2003/0208266 | A1 | 11/2003 | Tsai | 623/5 |
| 2004/0009590 | A1 | 1/2004 | Tan et al. | 435/366 |
| 2005/0026279 | A1 | 2/2005 | Tseng | 435/378 |

FOREIGN PATENT DOCUMENTS

| | | |
|---|---|---|
| GB | 2110531 A | 6/1983 |
| WO | WO03018040 A1 * | 3/2003 |

OTHER PUBLICATIONS

Dutt et al. 1991 Extracellular matrix mediated growth and differentiation in human pigment epithelial cell line 0041. Curr Eye Res. Dec. 1991;10(12):1089-100. (Abstract only).*
Dutt et al. 1991. Extracellular matrix mediated growth and differentiation in human pigment epithelial cell line 0041. Current Eye Research. 10(12):1089-1100.*
Dua et al. 1999. Amniotic membrane transplantation. Br. J. Ophthalmol. 83:748-752.*
Grueterich et al. 2002. Connexin 43 expression and proliferation of human limbal epithelium on intact and denuded amniotic membrane. Invest. Ophthalmol. Vis. Sci. 43:63-71.*
Justia.com. 2008. US 40 C.F.R.§141.2. Definition. http://law.justia.com/us/cfr/title40/40-22.0.1.1.3.1.16.2.html. p. 1-9.*
Merriam-Webster online dictionary. 2008. Definition of "confluent" http://www.merriam-webster.com/dictionary/confluent. p. 1-2.*
Snodderly et al. 2002. Retinal Pigment Epithelial Cell Distribution in Central Retina of Rhesus Monkeys.Investigative Ophthalmology & Visual Science, Sep. 2002, vol. 43, No. 9; p. 2815-2818.*
Robb. 1985. Regional Changes in Retinal Pigment Epithelial Cell Density During Ocular Development. Invest Ophthalmol Vis Sci 26:614-620.*
International Search Report dated Jan. 25, 2005, for PCT/US03/31464 (3 sheets), Notification of Transmittal (1 pg.), Cover sheet of WO 2004/033635 A3.

(Continued)

*Primary Examiner*—Taeyoon Kim
(74) *Attorney, Agent, or Firm*—Wilson Sonsini Goodrich & Rosati

(57) ABSTRACT

The present invention relates to a composition for implantation in the subretinal space of an eye, the composition including amniotic membrane, which may be cryopreserved human amniotic membrane, and a plurality of retinal pigment epithelial (RPE) cells or RPE equivalent cells present at the amniotic membrane. The amniotic membrane may be intact, epithelially denuded, or otherwise treated. The invention includes the use of amniotic membrane for the culturing of RPE cells thereon, forming a surgical graft for replacement of Bruch's membrane as a substrate, and for the transplanting of RPE cells to the subretinal space. The composition does not elicit immunological reactions to alloantigens or to RPE specific autoantigens; and exerts anti-inflammatory, and angiogentic, and anti-scarring effects. The invention includes methods and kits for making or using composites including amniotic membrane and RPE cells. Also disclosed is a device for harvesting RPE cells.

15 Claims, 2 Drawing Sheets

OTHER PUBLICATIONS

Binder, S., et al., "Transplantation of Autologous Retinal Pigment Epithelium in Eyes With Foveal Neovascularization Resulting From Age-Related Macular Degeneration: A Pilot Study," *Am J Ophthalmol*, 133(2): 215-25 (2002).

Phillips, S.J., et al., "Autologous Transplantation of Retinal Pigment Epithelium After Mechanical Debridement of Bruch's Membrane," *Invest Ophthalmol Vis Sci.*, In Press 1-11 (2002).

Pfeffer, B.A., "Improved Methodology for Cell Culture of Human and Monkey Retinal Pigment Epithelium," *Prog. Retin. Eye Res.*, Chapter10: 251-91 (1991).

Flood, M.T., et al., "Growth Characteristics and Ultrastructure of Human Retinal Pigment Epithelium in Vitro," *Invest Ophthalmol Vis Sci.*, 19:1309-20 (1980).

Hu, J., Bok, D., "A cell culture medium that supports the differentiation of human retinal epithelium into functionally polarized monolayers," *Molecular Vision*, 7:14-19 (2000).

Dutt, K, et al., "Extracellular matrix mediated growth and differentiation in human pigment epithelial cell line 0041," *Current Eye Research*, 10 (12): 1089-100 (1991).

Lu, L., et al., "Retinal pigment epithelium engineering using synthetic biodegradable polymers," *Biomaterials*, 22: 3345-55 (2001).

Kim, J.C., Tseng, S.C.G., "Transplantation of Preserved Human Amniotic Membrane for Surface Reconstruction in Severely Damaged Rabbit Corneas," *Cornea*, 14:473-84 (1995).

Tezel, T.H., et al., "Fate of Human Retinal Pigment Epithelial Cells Seeded onto Layers of Human Bruch's Membrane," *Invest. Ophthalmol.Vis.Sci.*, 40:467-76 (1999).

Dua, H.S., Azuara-Blanco, A., "Amniotic membrane transplantation," *Br.J.Ophthalmol*, 83:748-52 (1999).

Grueterich, M., Espana, E., Tseng, S.C.G., "Connexin 43 Expression and Proliferation of Human Limbal Epithelium on Intact and Denuded Amniotic Membrane," *Invest Ophthalmol Vis.Sci*, 43:63-71 (2002).

Meller, D., Tseng, S.C.G., "Conjunctival Epithelial Cell Differentiation on Amniotic Membrane," *Invest. Ophthalmol. Vis. Sci.*, 40:878-86 (1999).

Lu, L., et al., "Retinal pigment epithelium cell culture on thin biodegradable poly(DL-lactic-co-glycolic acid) films," *J Biomater. Sci. Polymer Edn.*, 9(11):1187-205 (1998).

Singh, S., et al., "Natural and artificial substrates for retinal pigment epithelial monolayer transplantation," *Biomaterials*, 22:3337-343 (2001).

DelPriore, L., Tezel, T., "Reattachment Rate of Human Retinal Pigment Epithelium to Layers of Human Bruch's Membrane," *Arch Ophthalmol*, 116: 335-41 (1998).

Koizumi, N., et al., "Cultivation of Corneal Epithelial Cells on Intact and Denuded Human Amniotic Membrane," *Invest. Ophthalmol. Vis. Sci.*, 41(9):2506-513 (Aug. 2000).

Koizumi, N., et al., "Amniotic Membrane as a Substrate for Cultivating Limbal Corneal Epithelial Cells for Autologous Transplantation in Rabbits," *Cornea*, 19(1):65-71 (2000).

Koizumi, N., et al., "An Evaluation of Cultivated Corneal Limbal Epithelial Cells, Using Cell-Suspension Culture," *Invest. Ophthalmol. Vis. Sci.*, 43 (7): 2114-121 (Jul. 2002).

Gruetrich, M., Tseng,S.C.G., "Human Limbal Progenitor Cells Expanded on Intact Amniotic Membrane Ex Vivo," *Arch Ophthalmol*, 120:783-90 (Jun. 2002).

Espana, E., et al., "Human Keratocytes Cultured on Amniotic Membrane Stroma Preserve Morphology and Express Keratocan," *Invest. Ophthalmol. Vis. Sci.*, 44(12):5136-141 (Dec. 2003).

Koh,S.-W., "VIP Enhances the Differentiation of Retinal Pigment Epithelium in Culture: from cAMP and pp60$^{c-src}$ to Melanogenesis and Development of Fluid Transport Capacity," *Progress in Retinal and Eye Research*, 19(6):669-88 (2000).

Albert, D.M., et al., "In Vitro Growth of Pure Cultures of Retinal Pigment Epithelium," *Arch Ophthalmol*, 88: 63-69 (1972).

* cited by examiner

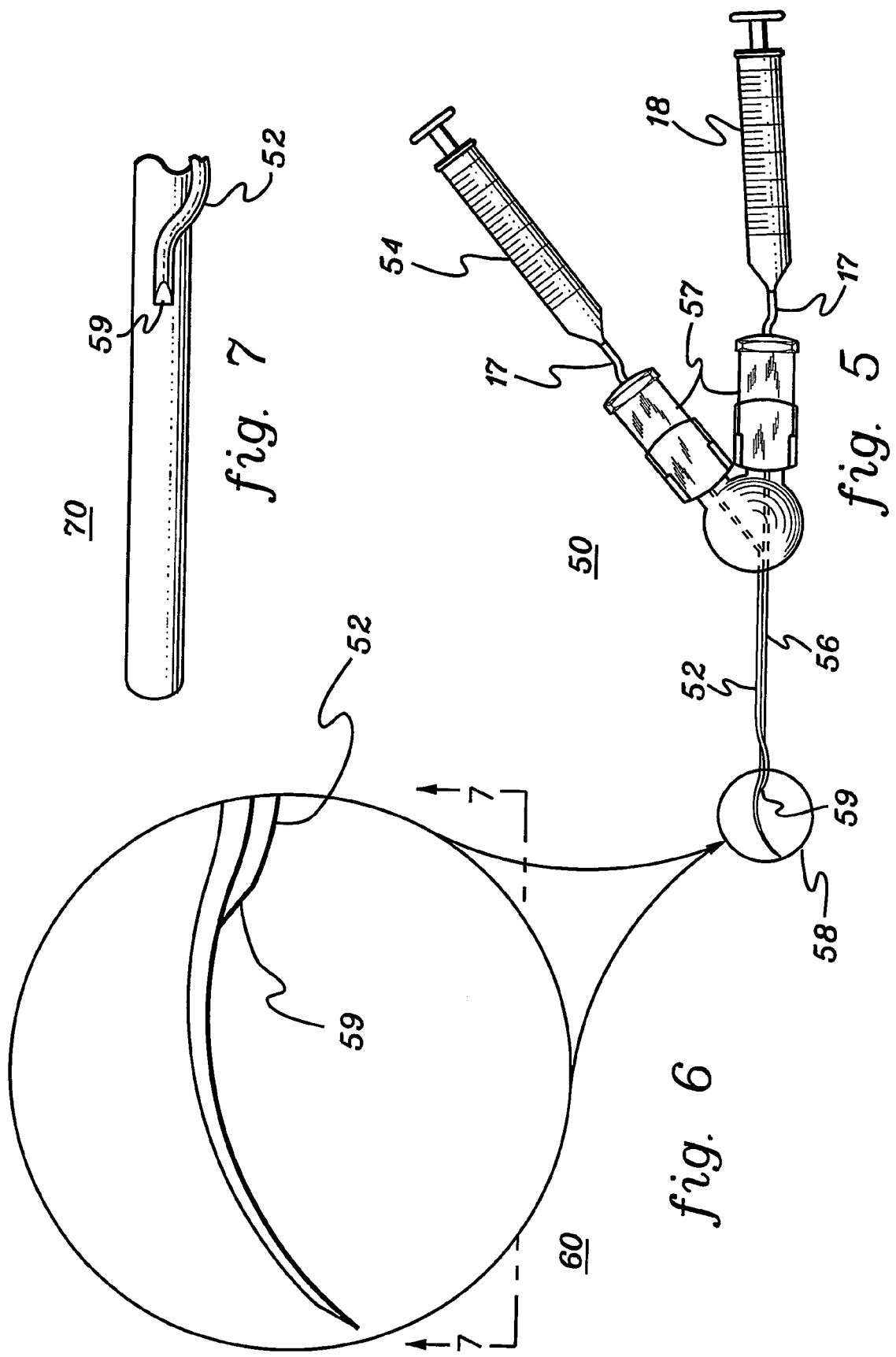

RETINAL PIGMENT EPITHELIAL CELL CULTURES ON AMNIOTIC MEMBRANE AND TRANSPLANTATION

RELATED APPLICATION

This application claims the benefit of U.S. Provisional Application No. 60/415,986 filed on 4 Oct. 2002, the teachings of which are incorporated herein by reference in their entirety.

BACKGROUND OF THE INVENTION

The retina is a multi-layered nervous tissue where light energy is converted into nerve impulses. The outermost layer of the retina, closest to the front of the eye, is a layer of neurons that includes ganglion cells. Behind the ganglion cells is a layer of integrating neurons, and behind the integrating neurons is a layer of photoreceptor cells, called rods and cones. Photoreception in rods and cones begins with absorption of light by a pigment in the cells, the absorbed light causing a receptor potential.

Forming an intimate structural and functional relationship with the photoreceptor cells is the retinal pigment epithelium, a monolayer of specialized, cuboidal cells located immediately behind the retina. The retinal pigment epithelial (RPE) cells provide support for the photoreceptor cells and carry on important physiological functions, including solute transport, phagocytosis and digestion of discarded outer segments of membranes shed from photoreceptor cells, and drug detoxication.

The RPE cells rest on a specialized basement membrane, called the Bruch's membrane, a membrane 1 to 5 microns in thickness and composed of collagen, laminin and other molecules.

Underlying the RPE cells is the choriocapillaris of the choroid tissue. The choriocapillaris contains the vasculature to provide nutrients and remove metabolic by-products from the retina. Underlying the choroid tissue is the sclera.

It is believed that failure of the RPE cells to properly perform their functions alters the extracellular environment for photoreceptor cells, and leads to the eventual degeneration and loss of photoreceptor cells. Dysfunction of RPE contributes to the pathogenesis of a variety of sight-threatening diseases including age-related macular degeneration (ARMD) 1, serious retinal detachment 2, and such genetic diseases as gyrate atrophy 3 and choroideremia 4.

Age-Related Macular Degeneration

ARMD is the leading cause of visual impairment in western countries and is believed to be caused by progressive deterioration of RPE, Bruch's membrane, and the choriocapillaris, which leads to subsequent damage to the photoreceptor cells. In ARMD, the RPE cells are dysfunctional. In one form of ARMD, degeneration of the RPE cells is followed by atrophy of the choriocapillaris. In another form, the Bruch's membrane is altered and degraded by invasion of choroid neovascular membrane (CNV) into the subretinal space, leading to hemorrhage in the subretinal space, and scarring, with possible further damage to both RPE and photoreceptors.

Although CNV invasion 5 into the subepithelial and/or subretinal space can be treated with laser photocoagulation, if neovascularization is subfoveal, the results are poor 6. Surgical removal of CNV membranes seldom leads to improvement of vision or halts the progression of ARMD 7. The poor results may be due to inadvertent removal of RPE during the CNV removal 8, the failure of RPE to re-populate, the progressive enlargement of choriocapillaris atrophy following submacular surgery 9, and photoreceptor loss.

Problems with Prior Art Methods of RPE Transplantation

Only limited success in restoring vision using current methods of RPE transplantation has been achieved with either autologous or allogeneic sources (experimental 6;10 and clinical 11-14). In experimental animals, in particular in the Royal College of Surgeons ARCS) Rat model of retinal degeneration 15-19, RPE transplantation has been used to rescue photoreceptors, preserve choriocapillaris, and prevent CNV. In the case of allogeneic RPE transplantation, one obvious reason to explain the failure is allograft rejection 13;20. However, in the case of autologous RPE transplantation, the failure to restore vision may be due to the failure of transplanted RPE to repopulate the diseased site or to function in vivo. The failure of the RPE to grow or to function may be due to damage to the Bruch's membrane.

The Bruch's Membrane

There is evidence that the integrity of Bruch's membrane is crucial for RPE repopulation and subsequent functions. For example, surgical removal of RPE without damage to Bruch's membrane results in partial regeneration of the RPE monolayer in the non-human primate and domestic pig with the preservation of the underlying choriocapillaris and the overlying photoreceptors 21-23. In contrast, abrasive debridement causes more damage to Bruch's membrane, leads to incomplete repopulation of RPE, choriocapillaris atrophy, and outer segment retinal degeneration 24. Experimental transplantation of cultured human RPE to Bruch's membrane of the owl's monkey eye results in normal attachment, viability, and expressing junctions and morphological polarity 25. Autologous transplantation of RPE onto an abrasively debrided Bruch's membrane decreases choriocapillaris atrophy and photoreceptor loss in rabbits 26.

In the case of human patients with ARMD, the failure of restoring RPE function in transplanted human autologous RPE may be at least partially due to the altering of Bruch's membrane intrinsically caused by ARMD 27 and damaged by surgical removal of CNV membrane 23;24.

The current method of RPE transplantation, subretinal injection of an RPE cell suspension, achieves a limited success. There are many problems associated with this method, including a resulting subretinal fibrosis and the formation of multiple layers of RPE 6. These problems may be due to lack of restoration of in vivo (normal) epithelial phenotype and function. To date, no advance has been made in restoring Bruch's membrane in the surgical treatment of ARMD.

Immunological Aspects of RPE Transplantation

Although the eye as a part of the central nervous system has characteristics of an immunologically privileged site, it has been demonstrated that RPE transplants sensitized their recipients to both alloantigens and to RPE-specific autoantigens. Both are considered potential barriers to successful transplantation, and would make immune suppression regimens necessary 28. It was also demonstrated that the immunological response is most likely related to the amount of transplanted cells and that the response increases with time. RPE allografts in the RCS rat were not rejected for up to one year.

Problems with Prior Art Substrates and Methods of Culturing RPE

Substrates that have been used for this purpose include plastic 31, cross-linked collagen 32, gelatin 1, fibrinogen 2, poly-L-lactic acid ELLA) 3, PLLA/PLGA (poly-DL-lactic-co-glycolic acid) film 5-6, hydrogel 7, and basement membrane-containing anterior lens capsule 7. There are many disadvantages associated with each of the prior art substrates used for culturing RPE cells for transplantation, and a number of problems remain unsolved.

Impermeable Substance

One attempt at RPE transplantation utilized RPE cells isolated from either the whole eye or from a biopsy with Dispase® (GodoShusei Co., Ltd., Tokyo, Japan), and seeded on an impermeable substrate such as the plastic dish 31. These cells were prepared as a dissociated cell suspension 6;10 or as a patch derived from fetus 11 before transplantation. These cells did not fully retain their epithelial morphology. Furthermore, pigmentation of melanolipofuscin granules rapidly disappears on plastic cultures 33.

Porous Support (Cross-Linked Collagen, Collagen, Gelatin, Fibrinogen, PLLA/PLGA, Hydrogels, CNV Membranes, Lens Capsule)

Cross-linked collagen, when used for transplantation, is damaging to the retina due to its thickness, poor permeability and inability to degrade 32. Although human RPE cells 34 seeded on collagen membrane produced a monolayer of cells that exhibited a measurable transepithelial resistance and electrical potential 35, the cells did not achieve the in vivo state of development and function.

Gelatin has been used as an embedding medium, but not as a substrate for attachment. Fibrinogen and PLLA microspheres are also not suitable for transplanting RPE as a single sheet when transplanted to the subretinal space 2;3. PLLA/PLGA films do provide the RPE monolayer sheet for transplantation, but in vitro cultures of human fetal RPE cells grown on these supports do not show pigmentation (melanogenesis) 5;6. Hydrogel also provides the RPE monolayer sheet for transplantation, but the resultant cell density and the cell tight junction determined by expression of ZO-1, is relatively low 7.

Human RPE cells have also been cultured on surgically excised CNV membranes from ARMD patients, but the culture forms multiple layers 36.

Although lens capsule is a basement membrane-containing, natural material, it is not an ideal substrate for RPE culture and transplantation. Anterior lens capsule has been used to grow RPE 7;8 and IPE 8, and to transplant RPE and IPE 8 with lens capsule to the subretinal space. Both hydrogel and lens capsule, when used as substrates for RPE cultures, do not allow pigmentation to form (or melanogenesis) by RPE cells in culture 7;8.

The inventors of the present subject matter attempted to use the lens capsule as an autologous substrate for RPE/IPE transplants. However, the tendency of the capsule to curl made this technique impracticable. The idea to use the posterior capsule, because it is thinner, was also abandoned, for a number of reasons. First, the posterior capsule is difficult to obtain during surgery, without putting the patient at a high risk. Secondly, no absorption or slow absorption of the lens capsule material might inhibit the survival of the transplanted RPE cells because of insufficient contact of the cells with the Bruch's membrane and/or choriocapillaris.

Recently Bilbao et al, 37 disclosed the use of PLGA, coated on one side of a lens capsule to prevent curling and to facilitate its use for subretinal release. However, histological studies showed not only that the PLGA had completely dissolved after 4 weeks, but also that the overlying retinal layers were disrupted, the disruption accompanied by a large amount of cell infiltration.

Cryoprecipitate from blood donors was also tested as a possible autologous substrate for human fetal retinal pigment epithelium by Farrokh-Siar et al in 1999 (38). Dutt et al, 39 used several substrates for culture of BPE cell line 0041: extracts from placenta and amnion; MATRIGEL® (Collaborative Biomedical Products. Inc., Bedford, Mass.), a commercially available basement membrane matrix; dishes coated with extracellular matrix secreted by endothelial cells (ECM); dishes coated with collagen IV and/or laminin; dishes coated with collagen I and/or fibronectin. Although deeply pigmented, cells grown on MATRIGEL® looked like fibroblasts.

As described above, problems that remain to be solved include, for example, maintenance of the morphology of the RPE phenotype in cultured and transplanted RPE cells; creation of a uniform monolayer of autologous RPE on a biocompatible substrate; improvement of the transplant technique to better cover the defect; overcoming immune rejection of RPE transplants due to both alloantigens and RPE-specific auto-antigens; and prevention of subretinal fibrosis following RPE transplantation.

Amniotic membrane is a biological membrane that lines the inner surface of the amniotic cavity and comprises a simple, cuboidal epithelium, a thick basement membrane, and an avascular mesenchymal layer containing hyaluronic acid. Amniotic membrane transplantation has been used for ocular surface reconstruction in the treatment of acute chemical and thermal burns of corneal tissue 53.

Overall, the medical need for a method of culturing RPE cells suitable for transplantation to the subretinal space, a suitable RPE transplant composite with actions to maintain the epithelial phenotype and exert anti-inflammatory, anti-scarring, and anti-angiogenic effects to the underlying stroma, and a method of transplanting RPE cells to the subretinal space, has not been met.

SUMMARY OF THE INVENTION

The present invention relates, in one aspect, to the discovery that cryopreserved amniotic membrane, when appropriately procured and processed, can be used for the culturing of RPE cells or RPE equivalent cells thereon, and as a surgical graft for replacement of Bruch's membrane as a substrate, and for the transplanting of RPE cells or RPE equivalent cells to the subretinal space; and that the graft does not elicit immunological reactions. The invention relates, in one aspect, to compositions for implantation in the subretinal space of an eye of a patient in need thereof, the composition including amniotic membrane and RPE cells or RPE equivalent cells. In one embodiment of the invention, the amniotic membrane present in the composite is human amniotic membrane. The amniotic membrane may be intact, epithelially denuded, or otherwise treated. In one embodiment of the invention, the membrane is treated on one side, for example to thin or remove one side. In another embodiment, the amniotic membrane is reshaped by laser ablation to remove the stromal side or to thin the basement membrane side. In yet another embodiment mesenchymal cells are added to the stromal side. The invention, inter alia, comprises the following, alone or in combination.

One embodiment of the invention includes a composite comprising amniotic membrane; and a plurality of retinal pigment epithelial cells or retinal pigment epithelial equivalent cells present at the amniotic membrane.

Another embodiment includes a kit comprising amniotic membrane; a plurality of retinal pigment epithelial cells or retinal pigment epithelial equivalent cells present at the amniotic membrane; a buffer medium or a culture medium; and optionally, instructions for simultaneous, separate, or sequential use of at least one component of the kit for treating a retinal disease. In one embodiment, the amniotic membrane included in the kit is human amniotic membrane.

Another embodiment of the invention is a method of forming a composite, the method comprising the steps of applying at least one retinal pigment epithelial cell or retinal pigment epithelial equivalent cell to an amniotic membrane; and culturing the retinal pigment epithelial cell or retinal pigment epithelial equivalent cell on the membrane under conditions suitable for growth for a period of time sufficient to produce a plurality of cultured cells. The amniotic membrane used in one embodiment may be human. In one embodiment, the composite comprising cultured RPE cells or cultured RPE equivalent cells and amniotic membrane is used for implantation in the subretinal space of an eye of a host in need thereof. The host may be any mammal, for example, a human.

In yet another aspect, an embodiment of the invention includes a method of inducing an excised or cultured retinal pigment epithelial cell or retinal pigment epithelial equivalent cell to express or to maintain the phenotype of retinal pigment epithelial cells, the method comprising the steps of contacting amniotic membrane with the retinal pigment epithelial cell or retinal pigment epithelial equivalent cell; culturing the retinal pigment epithelial cell or retinal pigment epithelial equivalent cell on the membrane under conditions suitable for growth for a period of time sufficient to produce a plurality of cultured cells; and either contacting the cultured cells with an effective amount of an agent that raises the intracellular calcium ion concentration to a level sufficient to induce or maintain the phenotype of retinal pigment epithelial cells; or exposing the membrane comprising the cultured cells to an air-fluid interface for a period of time sufficient to induce or maintain the phenotype of retinal pigment epithelial cells. The amniotic membrane used in an embodiment may be human.

In one embodiment, both the step of contacting the cultured cells with an agent that increases the intracellular calcium ion concentration, and the step of exposing the membrane including the cultured cells to an air-fluid interface to induce or maintain the phenotype of retinal pigment epithelial cells, are performed sequentially or essentially simultaneously. However, in another embodiment, the medium can comprise either a normal or a high $Ca^{2+}$ concentration with growth factors added.

The present invention also relates, in yet another aspect, to the use of amniotic membrane to promote the growth and the differentiation of at least one retinal pigment epithelial equivalent cell to a plurality of cells that express the phenotype of retinal pigment epithelial cells. In a particular embodiment, the amniotic membrane is human.

Another embodiment of the invention is a method of delivering a plurality of retinal pigment epithelial cells to a target site in a subretinal space in an individual in need thereof, including the steps of forming at least one hole in a retina of the individual, or at least partially detaching the retina to access the subretinal space; inserting through the hole a composite including amniotic membrane and the retinal pigment epithelial cells present at the membrane; and positioning the composite at the target site.

The invention also relates to a method for treating a retinal disease, the method including inserting in a subretinal space of a patient in need thereof a composite comprising amniotic membrane, for example, human amniotic membrane, and a plurality of retinal pigment epithelial cells present at the membrane. The RPE cells may be cultured on the membrane according to a method of the invention. Non-limiting examples of retinal diseases that are treated according to an embodiment of the invention are age-related macular degeneration, retinal degeneration, gyrate atrophy, and choroideremia.

Another aspect of the invention is the use of amniotic membrane, which in one embodiment is human in origin, and at least one retinal pigment epithelial cell, for the manufacture of a composition for treatment of a retinal disease in a patient suffering from, or at risk of developing the disease.

The invention also relates to the use of human amniotic membrane to promote growth and differentiation of at least one retinal pigment epithelial equivalent cell to a plurality of cells that express the phenotype of retinal pigment epithelial cells.

Yet another aspect of the invention is the use of amniotic membrane for transplanting retinal pigment epithelial cells or iris pigment epithelial cells to a subretinal space, to prevent or decrease a sensitizing of a recipient to alloantigens and to retinal pigment epithelial-specific autoantigens. In a particular embodiment, the amniotic membrane used in transplanting RPE cells or IPE cells to a subretinal space, to prevent or decrease a sensitizing of a recipient to alloantigens and to retinal pigment epithelial-specific autoantigens is human in origin.

The invention also relates to the use of amniotic membrane, including human amniotic membrane, to inhibit fibrosis following transplantation of RPE cells or iris pigment epithelial (IPE) cells to the subretinal space. Another embodiment of the invention is the use of human amniotic membrane and at least one RPE cell for the manufacture of a composition for treatment of a retinal disease in a patient suffering from, or at risk of developing the disease.

Many advantages are obtained by the use of amniotic membrane, processed and cryopreserved according to an embodiment of the invention, as a substrate for the culturing of RPE or RPE equivalent cells thereon. For example, a composite comprising the amniotic membrane and RPE or RPE equivalent cells can be used as a surgical graft for substrate replacement and the transplanting of RPE cells in the subretinal space. The composite exerts anti-inflammatory, anti-angiogenic, anti-fiberoptic, and anti-scarring effects, and does not elicit immunological reactions to either alloantigens or RPE-specific auto-antigens. Further, amniotic membrane used according to an embodiment of the invention promotes growth and differentiation of RPE cells in culture, and maintenance of the morphological appearance of the RPE cells both in culture and following transplantation to the subretinal space. The composite and method of delivery of RPE cells to the subretinal space result in a uniform monolayer of RPE cells on a biocompatible substrate having a basement membrane. A composite according to an embodiment of the invention can be used as a surgical graft suitable for replacement of Bruch's membrane as a substitute and for the transplanting of RPE cells to the subretinal space. Embodiments of the invention provide an improved transplant composite and technique to better cover the defect; to overcome immune rejection of RPE transplants due to both alloantigens and RPE-specific auto-antigens; to prevent sub-retinal fibrosis following RPE transplantation.

BRIEF DESCRIPTION OF THE DRAWINGS

The foregoing and other objects, features and advantages of the invention will be apparent from the following more particular description of illustrative embodiments of the invention, as illustrated in the accompanying drawings.

FIG. 5 is a side elevation view of another embodiment of an RPE harvesting cannula 50 with auxiliary infusion line 52.

FIG. 6 is an enlarged detailed view 60 of distal of 58 of cannula 50.

FIG. 7 is a bottom view 70 of distal of 58 of cannula 50 taken at view 7-7 of FIG. 6.

DETAILED DESCRIPTION OF EMBODIMENTS OF THE INVENTION

Figure 1:
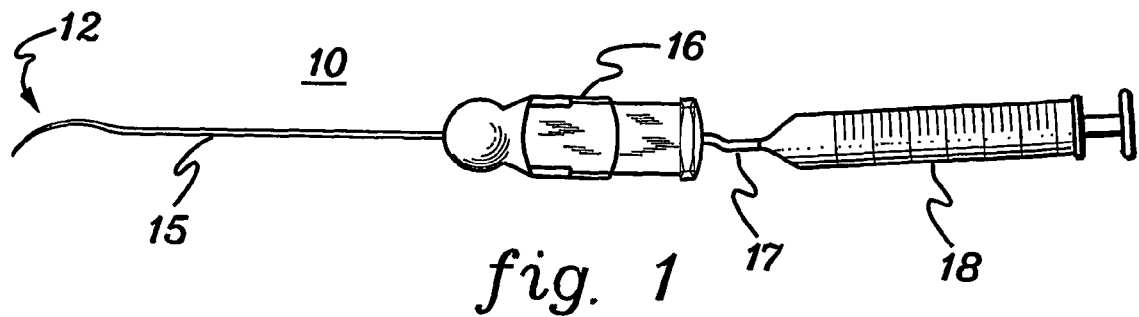
FIG. 1 is a side elevation view of RPE harvesting cannula 10.

A description of illustrative embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The inventors of the subject matter of the present invention attempted first to use the stromal side of amniotic membrane as a substrate on which to grow human umbilical vascular endothelial cells, but the cells would not grow on amniotic membrane. In fact, the endothelial cells underwent apoptosis. The inventors also used the stromal side of amniotic membrane as a substrate in an attempt to grow human polymorphonuclear leucocytes thereon, but the leucocytes would not grow on amniotic membrane.

The invention relates to the discovery that, under suitable conditions, RPE cells, RPE equivalent cells, and IPE cells will grow on appropriately procured and processed, cryopreserved amniotic membrane, for example, human amniotic membrane. Histologically, amniotic membrane comprises a thick basement membrane and an avascular stroma. The inventors have discovered that human amniotic membrane is an ideal extracellular matrix substrate to promote growth and differentiation of RPE equivalent cells and RPE cells in culture.

The RPE cells, RPE equivalent cells, and IPE cells grown on amniotic membrane under suitable conditions, differentiate, tend to retain their morphological characteristics, and do not tend to de-differentiate. Further, the amniotic membrane with the cells present thereon can be used as a surgical graft to transplant RPE cells to the subretinal space, and for substrate replacement. The graft does not elicit immunological reactions, and can be used to treat retinal diseases.

Accordingly, the invention relates to the resulting composite, including amniotic membrane, and a plurality of RPE, RPE-equivalent cells, or IPE cells, and to a method of use of the composite as a surgical graft to transplant RPE to the subretinal space of a mammalian eye in order to treat retinal diseases such as age-related macular degeneration, retinal degeneration, gyrate atrophy, and choroideremia.

RPE or RPE-equivalent Cells

The term, "RPE equivalent cells," as used herein, refers to cells that are derived from either retina, iris, ciliary body, adult stem cells or embryonic stem cells, and which either retain their normal phenotype or function; or which may have less than optimal function; or which have been induced in vitro or in vivo to differentiate into RPE cells.

According to an embodiment of the invention, the source of RPE cells can be from human or other mammals. According to another embodiment of the invention, the source of RPE cells can be either autologous (from the same individual as the recipient) or allogeneic (from a different individual from the recipient). For the latter, these cells can be either obtained from adult or fetal, cadaveric or living individuals, of which the latter can be BLA-matched or non-matched.

Further, the source of human RPE equivalent cells can be derived from retina or iris or ciliary body. The RPE cells, in one embodiment, comprise cells derived from neural retinal cells, for example, rod cells or cone cells. If derived from iris, the cells are termed iris pigment epithelial cells (IPE), and their function may be suboptimal. The source of human RPE equivalent cells can also be derived from RPE cells that have been immortalized by viral or non-viral agents but still retain normal phenotype or function.

The source of human RPE equivalent cells can also be derived from adult stem cells or embryonal stem cells, of which the differentiation into RPE has been induced in vitro. For the former, such adult stem cells can be obtained either autologously or allogeneically from various sites of the body, for example, from the peripheral blood or bone marrow.

The source of RPE equivalent cells can also be derived from other non-human species but bioengineered so that they become compatible with human cells. For example, a source of the retinal pigment epithelial equivalent cells used in a composite according to the invention may include at least one bioengineered cell induced in vitro to differentiate into a retinal pigment epithelial cell.

Harvesting of RPE Cells or RPE Equivalent Cells

If the source of RPE or IPE is autologous, the means of harvest will be surgical biopsy from the tissue site of retina or iris. Autologous RPE equivalent cells are derived from adult stem cells, and can be obtained from the site of interest, e.g., peripheral blood or bone marrow. If the source of RPE or IPE is allogeneic, either from a living individual, or cadaveric, they will be obtained form donated tissues, respectively. Other sources of allogenic RPE equivalent cells are well known to those of skill in the art of tissue culture and transplantation.

One method of harvesting or isolating RPE or IPE cells is conventional and includes non-enzymatic solutions containing EDTA or EGTA or enzymatic digestion using collagenase or DISPASE® solutions. The method of harvesting or isolating RPE equivalent cells induced from stem cells is performed in vitro using growth factors and inducible factors.

In yet another aspect of the invention, an embodiment of a device for harvesting RPE cells was conceived and designed. The device, referred to herein as the "Binder RPE harvester cannula", the "RPE harvester cannula", or "the cannula", minimizes damage to the RPE and maximizes harvest yield.

The device has several features and is described as follows. Referring now to the drawings, FIG. 1 shows an illustrative embodiment of a harvester cannula 10 having a syringe 18 attached by a flexible or bendable tubing 17 to a conventional, tapered LUER female connector fitting 16. An aspiration line 15 with a distal 12 is connected to the syringe 18 and passes through the LUER connector 16. In one embodiment, the outer diameter of the harvester cannula 10 is a standard 20 gauge (ga) (0.9 mm) at the sclerotomy site to match current vitrectomy instruments. Its proximal end may be terminated with a conventional LUER female connector fitting, and a short, for example, about 10 cm to about 20 cm long, flexible tube 17 connected to a glass syringe 18, for example, 0.5 cc capacity. The term "flexible" as used herein means that the tube described as "flexible" can be bent by a degree sufficient to manipulate the device during surgery. The flexible tube 17 is preferably made of non-stick material such as Teflon to prevent the adhesion of RPE cells to the inner wall and thus maximize harvesting.

Figure 2:
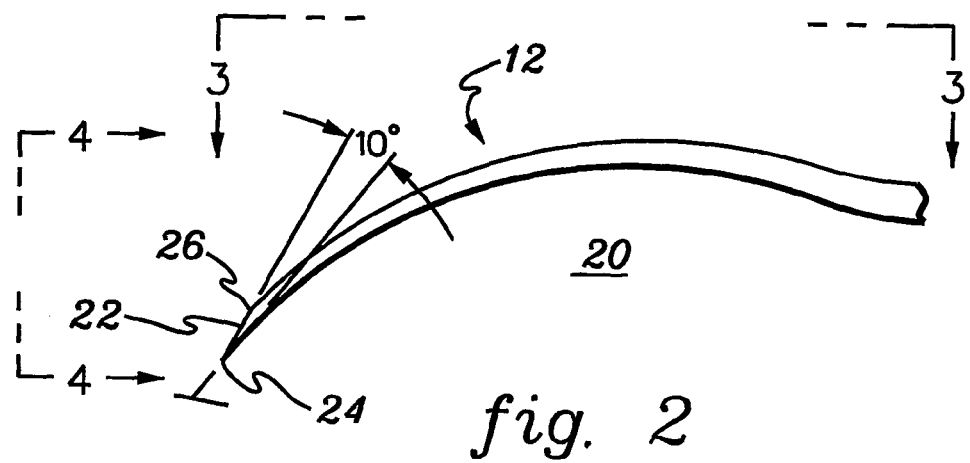
FIG. 2 is an enlarged detailed view 20 of distal 12 of cannula 10.
Figure 3:
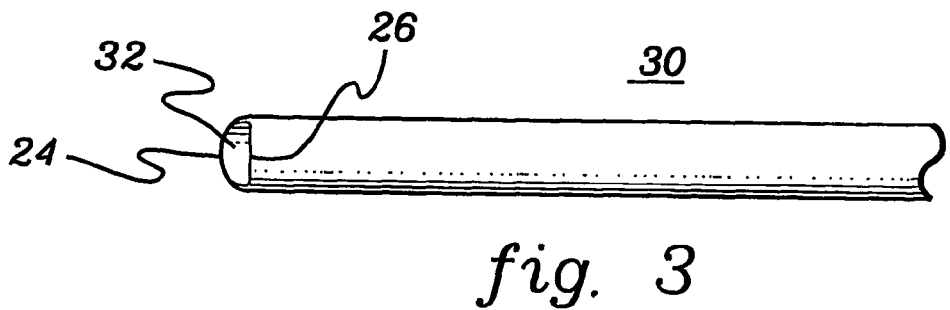
FIG. 3 is a view of FIG. 2 taken at view 3-3.
Figure 4:
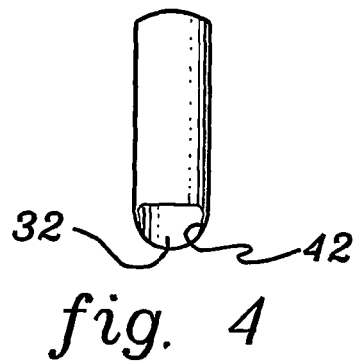
FIG. 4 is an end view of tip 12 of cannula 10 taken at view 4-4 of FIG. 2.

The cannula distal 12 is bent (for example, approximately a 10 mm radius of curvature). Approximately the last 5 mm of the distal tip 12, that will be placed in contact with the retinal tissues, has a flattened crescent-shaped hollowed cross-section with a radius of curvature matching the surface of Bruch's membrane at the posterior pole. That radius is 11 millimeters (mm) approximately. As shown in FIG. 2, an enlarged detailed view of distal of 12 of cannula 10 shows an approximately 10 degree taper on the end of tip 12 forming lower lip 26 and protruding upper lip 24. Therefore, as the cannula is used in surgery, the upper or higher lip protrudes forward and is visible at all times through the operation microscope (surgeon's view). FIG. 2 also shows directional views for FIGS. 3 and 4. When the cannula is in use, the protruding upper lip 24 is in contact with the retina, which is slightly lifted; and the lower lip 26 is in contact with RPE cells being collected.

In one embodiment, the thickness of each lip is approximately 75 micrometers; the hollow bore is of about 100 micrometers in height, making the thickness of the tip about 250 micrometers. The width of the cannula's outer surface at its distal end can be approximately 1.5 mm; the width of the hollow bore can be approximately 1.35 mm. In one embodiment, the upper or higher lip taper is finished with a smooth, polished round edge of approximately 3 micrometers. As the higher lip is slightly tapered, and as the retinal tissue is somewhat elastic or bendable, the retinotomy width needs to be only 1 mm approximately.

In one embodiment, the RPE harvester cannula has a flattened crescent shape with a forward protruding lip that can glide on the surface of the elastic Bruch's membrane supporting the RPE cells. This will maximize RPE cell harvesting over a width of approximately 1.2 mm per pass. As the posterior curvature of the cannula's lip matches that of Bruch's membrane, it will minimize damage to the membrane itself That is, little or no cutting, stripping or pitting can occur. Because its cross-sectional shape is similar to the length and shape of the retinotomy opening, a good fit will be obtained between the cannula outer wall and the edges of the retinotomy. This will minimize trauma to the retina and prevent or minimize backflush of RPE cells into the vitreous cavity. For example, in FIG. 3, a view of FIG. 2 taken at view 3-3 shows upper protruding lip 24, lower lip 26, of a hollow in-tube 30 forming aspiration 32.

The RPE harvester cannula can be made of stainless steel and preferably of anti-stick plastic, such as Teflon-like materials. An illustrative embodiment utilizes chloro-trifluoroethylene (CTFE) plastic which has the advantage of being totally transparent, allowing the surgeon to see the content of the cannula's inner bore.

Another embodiment of the RPE harvesting cannula 50, shown in FIG. 5, has an aspiration line 56, and an auxiliary infusion line 52 connected to its upper body. Line 52 has an out-infusion 59 situated at the start of the curvature of the tip of the cannula. An infusion LUER 57 is connected to a 1 cc syringe 54 via a short flexible or bendable line 17. In use, when the tip of the harvesting cannula is beneath the retina, a short pulse-like bolus of saline is injected from syringe 54, through infusion line 52, which may be made of stainless steel and soldered to the aspiration line 56. The bolus of saline lifts the retina and thus forms a bleb, that is, a space or tent under the retina, allowing the surgeon to harvest RPE cells with greater ease. If not used, the infusion 59 should be closed by a LUER plug to prevent back-flush.

FIG. 6 shows an enlarged view 60 of distal of 58 of cannula 50 showing the same profile as FIG. 2 with the addition of infusion line 52 and infusion 59.

FIG. 7 is a bottom view 70 of distal of 58 of cannula 50 taken at view 7-7 of FIG. 6, and showing added infusion line 52 and out-infusion 59.

Method of Preparing Amniotic Membrane

Methods of preparing cryopreserved human amniotic membrane suitable for use in an embodiment of the invention are well known in the art and are described, for example in U.S. Pat. Nos. 6,152,142 and 6,326,019 B1 to Tseng, the teachings of each of which are incorporated herein by reference in their entireties. Methods of preservation of amniotic membrane are also described in WO 01/08716 A1, the teachings of which are incorporated herein by reference in their entirety. The amniotic membrane can also be freeze-dried.

Amniotic membrane suitable for use in an embodiment of the invention is obtained from mammalian placenta, especially human placenta, from which the chorion has been separated. The amniotic membrane used in an embodiment may also be derived, for example, from an equine, a bovine, or an alpaca source. Amniotic membrane suitable for use in an embodiment of the invention generally includes an epithelial layer, a basement membrane, and a stroma, the combination of the three layers preferably having an average total thickness of about 200 µm. Sheets of the amniotic membrane can be cut to size, mounted on filter paper, and stored in a storage solution. Such sheets can also be cut to size without being mounted on filter paper so long as the side of the surface is marked. If freeze-dried, the freeze-dried sheet is not stored in a solution. The storage solution comprises a culture medium and a hyperosmotic agent, wherein the hydration of the amniotic membrane is maintained. The membrane can be impregnated with therapeutic agents, prior to storage or prior to use.

For use in an embodiment of the invention, the amniotic membrane is either intact (i.e., without additional treatments) or epithelially denuded (i.e., by EDTA and mechanical means as reported previously 62). See, Grueterich M, Espana E, Tseng SCG; Connexin 43 expression and proliferation of human limbal epithelium on intact and denuded amniotic membrane, *Invest Ophthalmol Vis. Sci.*, 43:63-71 (2002), incorporated herein by reference in its entirety. The amniotic membrane is either intact or ablated to remove the stromal portion on the stromal surface. If the epithelially denuded membrane is to be used, the denuded membrane is prepared before being seeded with RPE or RPE equivalent cells in culture (see below). However, if the amniotic membrane stroma is to be thinned, the stroma should be ablated either before or after such culturing. The method of ablation can be laser-driven, for example, by excimer laser. In other embodiments, the amniotic membrane can be treated to enable the RPE cells to better adhere to the membrane. For example, the membrane can be treated to produce an electrical charge thereon.

Method of Culturing RPE or RPE Equivalent Cells on Amniotic Membrane

After harvesting, the RPE or RPE equivalent cells are cultured in a medium containing culturing supplement including serum and growth factors. In one embodiment, the medium comprises a low $Ca^{2+}$ concentration from about 0.01 millimolar (mM) to about 0.4 mM preferably 0.1 mM. In another embodiment, the medium can comprise a normal or a high $Ca^{2+}$ concentration with growth factors added. The expansion culture is performed on a culturing substrate of choice. According to an embodiment of the invention, the expansion culture is performed on cryopreserved amniotic membrane.

A standard culturing method is used according to an embodiment of the invention. Cell seeding density can be varied depending on the surface area of amniotic membrane used. RPE or RPE equivalent cells are generally removed from a plastic substrate when they reach the subconfluent stage by conventional methods utilizing trypsin and/or EDTA. The isolated RPE or RPE equivalent cells are seeded on the amniotic membrane on the epithelial side, with the basement membrane either exposed or still covered by intact amniotic epithelial cells.

Methods of Inducing Epithelioid Phenotype in Culture of RPE on Amniotic Membrane According to an embodiment of the method, the step of culturing the retinal pigment epithelial cell or retinal pigment epithelial equivalent cell on the membrane is continued until the cells reach confluence. Ideally, the number of retinal pigment epithelial cells present at the membrane is about 4000 cells per 1 $mm^2$. However, the ideal number will depend on the size of the defect to be covered with the transplanted composite. For example, from about 16,000 to about 20,000 cells with high vitality are needed to cover a 4 $mm^2$ defect.

One method according to an embodiment of the invention, of inducing epithelial phenotype from a fibroblastic phenotype of RPE, is to elevate calcium concentration from low (for example, a range of from about 0.01 to about 0.4 mM, preferably about 0.1 mM) to high in the range of from about 0.5 to about 2.0 mM, preferably about 1.8 mM. The calcium ion concentration may be elevated, according to an embodiment, by adding a soluble calcium salt to the culture medium. Alternatively, an agent such as a calcium ionophore, which facilitates transport of calcium ion across the lipid barrier of the cell membrane by combining with the ion or by increasing the permeability of the barrier to the ion may be used to increase $Ca^{2+}$ concentration. Another embodiment includes an agent that increases intracellular calcium concentration by blocking the export of $Ca^{2+}$ out of the cytoplasm. In another embodiment, the medium can comprise a normal or a high $Ca^{2+}$ concentration with growth factors added. According to another embodiment, the amniotic membrane comprising RPE or RPE equivalent cells cultured thereon is exposed to air-fluid interface. A combination of methods can also be employed, either simultaneously or sequentially.

The Composite Including RPE Cells or RPE Equivalent Cells on Amniotic Membrane

According to one embodiment, a composite includes intact human amniotic membrane comprising a basement membrane and a stroma. In another embodiment of the invention, the human amniotic membrane of the composite is epithelially denuded.

The invention also relates to a composite that further includes at least one pharmaceutically active molecule. In one embodiment of the invention, the pharmaceutically active molecule in the composite is one or more of the following: a growth factor, an enzyme, or a therapeutic drug.

A Kit for Treating Retinal Disease

Another embodiment includes a kit comprising amniotic membrane, which may be human amniotic membrane; a plurality of retinal pigment epithelial cells or retinal pigment epithelial equivalent cells present at the amniotic membrane; a buffer medium or a culture medium; and optionally, instructions for simultaneous, separate, or sequential use of at least one component of the kit for treating a retinal disease. In a particular embodiment, the kit further includes at least one pharmaceutically active agent. The agent may include growth factors, enzymes, and therapeutic drugs. The growth factor may include retinal pigment epithelium-derived growth factor and/or transforming growth factor-beta. The agent may include interleukin-10. The agent may be present on the composite, or separately packaged, to be added to the composite or to the target tissue site in the subretinal space prior to implantation, or to be administered to the patient subsequent to transplantation.

The kit according to an embodiment may include retinal pigment epithelial equivalent cells that are bioengineered cells.

The kit according to an embodiment may include a composite formed of amniotic membrane and retinal pigment epithelial equivalent cells of autologous origin that have been previously harvested from the intended recipient, sent to a laboratory wherein the cells are cultured on amniotic membrane, and added into the composite.

Method of Transplant of RPE Cells to the Subretinal Space

The surgical procedure for transplant of RPE is similar to standard procedure for intraocular surgery. The procedure comprises the following steps:
a) Pars plana vitrectomy and removal of the posterior hyaloid membrane;
b) The first retinotomy is performed temporally or nasally superior to the CNV membrane;
c) Using Ringer's solution, the submacular CNV membrane is gently hydro-dissected and removed with a sub-retinal forceps. During this step, the intraocular pressure is elevated, and Perfluorocarbon (PFCL) is used to prevent or minimize bleeding.
d) The intraocular pressure is lowered to about 15 to about 20 millimeters (mm)Hg, and a shallow retinal detachment is created, if not present, by sub-retinal injection with Ringer's solution;
e) With the help of either an injection system or a specially made forceps having very smooth surfaces, such as, for example, mirror-finish or anti-stick Teflon surfaces, the prepared sheet of amniotic membrane with RPE monolayer is delivered into the sub-retinal area in the foveal area;
f) Finally, an air or gas tamponade is made to secure the transplant sheet in position; the scierotomies are closed; and the patient is asked to remain in a prone position for the next few days.

With regard to the forceps that can be used in step "e", it should be noted that unmodified, commercially available forceps cannot be easily used to transfer the amniotic membrane-RPE implant to a location under the retina, because the membrane sticks to stainless steel so well that the implant cannot be released. Therefore, the jaws should be coated with a Teflon®-like substance. Note that the Teflon coated jaws must be mirror-finished as any micro asperities will attach or stick to the membrane, thereby preventing release of the membrane in the space surgically created between the retina and Bruch's membrane. A prototype forceps comprising chlorotrifluoroethylene (CTFE) instead of stainless steel is being made in our laboratory for use in the implantation of the amniotic membrane-RPE composite. CTFE has almost the same anti-stick properties of Teflon® and is transparent, allowing the surgeon to see through it. An additional advantage provided by the CTFE forceps is that because CTFE is more flexible and softer than stainless steel, the CTFE jaws will minimize trauma to the amniotic membrane-RPE implant. The forceps with flexible transparent CTFE jaws is about 20 gauge (ga).

For the CTFE forceps, we will use one of the many conventional mechanisms to actuate the jaws. These mechanisms are located in the handle or immediately in front of the handle which is connected to a tube that is about 35 to 50 mm long and has an external diameter of about 0.9 mm or less. The function of the tube is to facilitate passing the forceps through the sclerotomy incision. The tube is made long enough to reach the posterior pole of the eye. The eye is normally about 24 mm in length, but depending on the presence of conditions such as myopia, staphyloma, etc, may be 20 to 35 mm in length. When closed, the jaws have a diameter equal to or a little less than the outer diameter of the tube.

Compressing the handle either retracts the jaws into the tube, thereby closing the jaws; or moves the tube forward, thereby closing the jaws. If the tube is moved forward, the tip of the jaws remains at a constant distance from the tissues or object being held. In some handles, a rotating knob located either on the distal end of the handle or immediately in front of it allows for rotation of the jaws. Other handles are round and can be easily turned around using one hand. As surgeons have individual preferences for handles, we will manufacture both types. All handles are commercially available (e.g., Storz-B&L Inc, Katena Inc, DORC Inc, Grieshaber-Alcon Inc, etc), but the CTFE jaws are not.

Alternatively, in step "e", an injection system can be used in lieu of the use of forceps to deliver the prepared sheet of amniotic membrane with RPE cells to the sub-retinal area.

It should be noted that, for cell harvesting only, a second retinotomy on the nasal side of the retina is performed.

EXEMPLIFICATION

Animals

Dutch belted rabbits were obtained from Covance Research Products, Inc. (Denver, Pa., USA). All rabbits used were euthanised by intramuscular injection of 0.3 ml ketamine (35 mg/kg) and xylazine (5 mg/kg) followed by an injection of 1 ml of Euthasol® (Delmarva Laboratories, Inc., Midlothian, Va.).

Materials

Dulbecco's modified Eagle's medium with F12 nutrient mixture 1:1 (V/V), dialyzed fetal bovine serum (FBS) with molecular cut off rate of 10,000 daltons, L-glutamine, L-methionine, L-lysine, L-leucine, magnesium chloride, magnesium sulfate, calcium chloride, cell culture grade water, sodium bicarbonate, FITC-conjugated goat anti rabbit IgG, and mouse monoclonal anti-cytokeratin (CK) 18 (clone CY-90) were all obtained from Sigma-Aldrich Chemical Company (St. Louis, Mo., USA). Phenol red sodium, DMEM/F12, sterile phosphate buffered saline (PBS), amphotericin B, trypan blue stain solution, and trypsin/EDTA were purchased from Gibco BRL (Grand Island, N.Y., USA). Twenty-four well plates were used. (Corning Life Sciences) Collagenase type 1 with 239 U/mg was purchased from Worthington Biochemical Corporation (Lakewood, N.J., USA). Penicillin and streptomycin were obtained from Bio Whittaker (Walkersville, Md., USA). Goat anti-rat Alexa 546-conjugated IgG (H+L), F(ab)2, Goat anti-mouse Alexa 488-conjugated IgG F(ab)2 were purchased from Molecular Probes Inc. (Eugene, Oreg., USA). Aqua-Poly/mount, was obtained from Polysciences Inc. (Warrington, Pa., USA). The polyclonal rabbit anti-RPE-65 antibody was a generous gift from T. Michael Redmond. The monoclonal rat anti-ZO-1 antibody (MAB 1520) was obtained from Chemicon (Temecula, Calif., USA). The monoclonal mouse anti-Pancytokeratin K8.13 Ab was obtained from ICN Biomedicals, Inc. (Aurora, Ohio, USA). As previously published 13, for the epithelial denudement of the amniotic membrane a corneal epithelial scrubber was employed (Amoils Epithelial Scrubber; Innova, Innovative Excimer Solutions, Inc., Toronto, Ontario, Canada). Culture plate inserts used for fastening amniotic membrane were from Millipore (Bedford, Mass., USA).

Primary RPE Cultures

Following euthanasia, eyes were immediately enucleated, and the anterior segment was removed by circumferential incision with scissors ca. 3-4 mm posterior to the corneal limbus. The isolation of RPE followed what has been reported 48 except that collagenase was used. In brief, the neural retina was detached by subretinal injection of sterile PBS, pH 7.4, to facilitate the removal of the vitreous residues and the neural retina. The RPE surface was then rinsed 3 times with PBS, and the eyecup was incubated with 1 mg/ml collagenase type 1 in DMEM/F12 for 1 h at 37° C. in the incubator with 5% CO2. RPE sheets were collected by gentle shaving of the Bruch's membrane with a heat-polished glass pipette. The cells were centrifuged at 800 rpm for 5 min and plated into 24 well plates (5-6 wells per eye) in DMEM/F12 adjusted to 0.1 mM $Ca^{2+}$, supplemented with 10% dialyzed FBS, 100 IU/ml Penicilin, (100 g/ml streptomycin and 0.5 g/ml amphotericin B). The cultures were cleared of the debris 48 h after plating by changing 50% of the medium with a fresh medium. The medium was then completely changed biweekly.

Amniotic Membrane Preparation

Human amniotic membrane (AM was kindly provided by Bio-Tissue, Inc. (Miami, Fla.) according to the method previously described (U.S. Pat. Nos. 6,152,142 and 6,326,019), and stored in DMEM and glycerol (1:1) at −80° C. before use. Upon use, AM was thawed at room temperature and rinsed with sterile Hanks Balanced Salt Solution (HBSS) to remove excess glycerol, and sutured with 4-0 silk surgical sutures (Alcon Surgical, USA) and/or tightened by a rubber-ring with the epithelial side facing up to 24 well plate culture insert as previously described 63. In a separate experiment, AM was epithelially denuded by incubation with sterile 0.02% EDTA in PBS for 45 min followed by gentle polishing with an epithelial scrubber (Amoils Epithelial Scrubber; Innova, Innovative Excimer Solutions, Inc., Toronto, Ontario, Canada) as previously described 62. After rinsing with sterile HBSS for 3 times, these AM were stored for 3 to 4 days in DMEM/F12 before seeding with RPE cells.

Passage of RPE Cells

First passage of RPE cells were obtained by the treatment of 0.05% trypsin and 0.02% EDTA in $Ca^{2+}$ and $Mg^{2+}$-free HBSS for 8 min when they were in the late log phase, and seeded at 5,000-20,000 viable RPE cells per cm2 (as assessed by trypan blue staining) in DMEM/F12 with $Ca^{2+}$ concentrations adjusted to 0.1 mM, and supplemented with 10% dialyzed FBS, 100 IU/ml PNS and 0.5 (μg/ml amphotericin B on either plastic, denuded AM or intact AM. Cells were left undisturbed for 36 h to allow attachment, and culture media were changed biweekly thereafter.

Calcium Switch

When RPE cells on each of the above culture reached confluence, the $Ca^{2+}$ concentration in the culture medium was changed to 1.8 mM by adding soluble calcium salt.

Evaluation

Each culture was followed with observation under a phase contrast microscope at 36 h after plating, at confluence, and one week and four weeks after the calcium switch. At different intervals, cultures were terminated by removing the medium, and rinsing the cells 3 times with sterile PBS. Thereafter, the cultures were fixed either in pre-cooled (−20° C.)

methanol for 5 min for Cytokeratins or in 4% paraformaldehyde at 4° C. for 10 min (for RPE-65, ZO-1). This was followed again by rinsing 3 times in PBS. The tissue was thereafter stored at 4° C. in 0.01 NaN3 in PBS for about 2 weeks until further processing. Primary antibodies were incubated overnight at 4° C. at the following concentrations: Pancytokeratin (K8.13) at 1/100, Cytokeratin 18 (CY-90) 1/3000 (both according to [25]), ZO-1 at 1/200 and the RPE-65 at 1/200. This was followed by 3 washes in PBS and then incubated for 2 h with respective secondary antibodies conjugated to either FITC (for RPE-65), Alexa 546 (for ZO-1), Alexa 488 (for Pancytokeratin and Cytokeratin 18) in a dilution of 1/200. All antibodies were diluted in PBS containing 1% BSA and 0.1% Triton x-100. The specimens were washed 3 times in PBS and mounted immediately in Aqua-Poly/mount mounting medium. The staining was then analyzed with a Zeiss Axiophot fluorescence microscope (Zeiss, Oberkochen, Germany) which was connected to a CCD Optronics camera. The images were subsequently enhanced with Adobe Photoshop 5.5 software. For immunostaining, the specificity of the above antibodies had been verified in dutch belted rabbit tissue. In brief, an animal, previously used for another procedure requiring subsequent euthanasia, was perfused under anaesthesia with 4% formaldehyde. Thereafter an injection of 4% paraformaldehyde in PBS was given intravitreally and the eye immersed in the same fixative and kept on ice for 2 h. The anterior segment was then dissected away and the vitreous removed as much as possible. Samples were cut with ophthalmic scissors from the posterior pole of the eye and the cornea, incubated in PBS with sequential sucrose gradients of 10, 20 and 30%, embedded in OCT and snap-frozen with liquid nitrogen. Tissue sections were cut at 8 μm on a Reichert Cryostat.

RESULTS

Morphological Appearance of RPE Grown in Low $Ca^{2+}$ on Different Substrates

Rabbit RPE cells were seeded at about 5,000 to about 20,000 viable RPE cells per $cm^2$ on plastic (P), epithelially denuded human amniotic membrane (dAM), or intact human amniotic membrane (iAM in low $Ca^{2+}$ DMEM/F12. Confluence was reached in about 7-9 days on dAM, which was faster than 9-10 days on plastic. RPE cells on these three cultures in general appeared spindle-shaped and were spread evenly on both substrates except that RPE cells on iAM appeared to be more squamous and polygonal and less evenly distributed when compared to the plastic culture and dAM when confluence was reached. Furthermore, pigmentation of melanolipofuscin granules rapidly disappeared on plastic cultures in part due to dilution by cell division, a phenomenon that has been well-recognized 33. Nevertheless, RPE cells on dAM still retained some granular appearance although pigmentation was also reduced, whereas RPE cells on iAM still possessed heavy pigmentation.

Morphological Appearance of RPE One Week After $Ca^{2+}$ Switch

When RPE cells reached confluence on dAM, the medium was switched to high $Ca^{2+}$ DMEM/F12. One week after $Ca^{2+}$ switch, RPE cells on plastic cultures remained spindle-shaped, but did not form clear granules except some pigmentation might reappear. In contrast, RPE cells grown on dAM adopted epithelioid appearance with a polygonal (hexagonal) shape, and exhibited abundant granules with pigmentation in the cytoplasm. RPE cells on iAM also adopted polygonal shape with heavy pigmentation. As a comparison, RPE cells grown on dAM and low calcium still retained spindle shape but appeared to have more pigmentation.

Characterization of Resultant Epithelial Phenotypes by Immunostaining

CK 18 Staining

Staining by antibody to CK 18 (cytokeratin 18), a marker to identify the epithelial origin of RPE cells, was performed. The results indicate that indeed RPE cultured on plastic under low $Ca^{2+}$ concentration had the epithelial origin because all cells were positive. RPE growing on intact and denuded membrane showed strong positive staining with vivid cytoskeleton pattern, that was more pronounced then the counterpart growing on plastic when $Ca^{2+}$ was elevated.

RP 65 Staining

Staining to RP65, a new marker for RP differentiation, was performed. A normal pattern of positive staining of RPE in vivo rabbit retina was obtained, the photograph of the staining showing a monolayer of RPE between the photoreceptors (on the top) and choriocapillaris (on the bottom), and the RPE cells were pigmented.

RP 65 Staining

RP65 staining showed that RPE grown on plastic was negative even 1.5 weeks after $Ca^{2+}$ switch. In contrast, RPE cells were strongly positive to RP 65 when grown on intact AM and on denuded AM. This result continued when the culture was extended to 3.5 weeks. The positive staining is shown by green fluorescence, while the reddish staining was nuclear counterstaining by PI.

ZO-1 Staining

ZO-1 staining is directed to the tight junction complex formed by RPE. In vivo, this antibody to ZO-1 showed positive (reddish fluorescence) in the RPE and photoreceptor complex. ZO-1 staining was also positive on the RPE cells grown on plastic and intact amniotic membrane, and on denuded AM.

REFERENCES

It is believed that surgeons, scientists and researchers will benefit from information provided in the following papers.

1. Young R W. Pathophysiology of age-related macular degeneration, *Surv. Ophthalmol,* 31:291-306 (1987).
2. Marmor M F. New hypothesis on the pathogenesis and treatment of serious retinal detachment, *Graefe's Arch. Clin. Exp. Ophthalmol,* 226:548-52 (1988).
3. Mitchell G A, Brody L C, Sipila I, Looney J E, Wong C, Engelhardt J F, et al., At least two mutant alleles of ornithine-D-aminotransferase cause gyrate atrophy of the choroid and retina, *Finns. Proc. Natl. Acad. Sci U.S.A,* 86:197-201 (1989).
4. Cremers F P M, van de Pol D J R K, van der Kerkhoff P M, Wieinga B, Ropers H R. Cloning a gene that is rearranged in patients with choroideremia, *Nature,* 347:674-7 (1990).
5. Green W R, Wilson D J. Choroid neovascularization, *Ophthalmology,* 93:1169-76 (1986).
6. Del Priore L V, Kaplan H J, Sivermann M S, Valentino T, Mason G, Hornbeck R. Experimental and surgical aspects of retinal pigment epithelial cell transplantation, *Eur. J. Implant Ref. Surg,* 5:128-32 (1993).
7. Thomas M A. in: Lewis H, Ryan S J, eds. *Medical and Surgical Retina.*, St. Louis: Mosby, 63-81 (1994).
8. Bynoe L A, Change T S, Funata M. Histopathologic examination of vascular patterns in subfoveal neovascular membranes, *Ophthalmology,* 101:112-7 (1994).

9. Castellarin A, Nasir M, Sugino K, Zarbin M A. Progressive choriocapillaris atrophy after surgery for age-related macular degeneration, *Retina*, 18:143-9 (1998).
10. Sheng Y, Gouras P, Cao H, Berglin L, Kjeldbye H, Lopez R, et al. Patch transplants of human fetal retinal pigment epithelium in rabbit and monkey retina, *Invest Ophthalmol Vis Sci.*, 36:381-90 (1995).
11. Algvere P V, Berglin L, Gouras P, Sheng Y. Transplantation of fetal retinal pigment epithelium in age-related macular degeneration with subfoveal neovascularization, *Graefe's Arch. Clin. Exp. Ophthalmol*, 232:707-16 (1994).
12. Marquardt T, Ashery-Padan R, Andrejewski N, Scardigli R, Guillemot F, Gruss P. Pax6 is required for the multipotent state of retinal progenitor Cells, *Cell*, 105:43-55 (2001).
13. Algvere P V, Gouras P. Long-term outcome of RPE allografts in non-immunosuppressed patients with AMD, *European J Ophthalmol*, 9:217-30 (1999).
14. Binder S, Stolba U, Krebs I, Kellner L. Transplantation of autologous retinal pigment epithelium in eyes with foveal neovascularization resulting from age-related macular degeneration: a pilot study, *Am J Ophthalmol*, 133:215-25 (2002).
15. Li L, Turner J E. Optimal conditions for long-term photoreceptor cell rescue in RCS rats; the necessity for healthy RPE transplants, *Exp. Eye Res.*, 52:669-79 (1991).
16. Little C W, Cox C. Correlates of photoreceptor rescue by transplantation of human fetal RPE in the RCS rat, *Exp. Neurol*, 149:151-60 (1998).
17. Little C W, Castillo B, Diloreto D A. Transplantation of human fetal retinal pigment epithelium rescues photoreceptor cells from degeneration in the royal college of surgeons rat retina, *Invest Ophthalmol Vis Sci.*, 37:204-11 (1996).
18. Seaton A D, Turner J E. RPE transplants stabilize retinal vasculature and prevent neovascularization in the RCS rat, *Invest Ophthalmol Vis Sci.*, 33:83-9 (1992).
19. Seaton A D, Sheedo H J, Turner J E. A primary role for RPE transplants in the inhibition and regression of neovascularization in the RCS rat, *Invest Ophthalmol Vis Sci.*, 35:162-9 (1994).
20. Weisz J M, Humayan M S, De Juan E. Allogeneic fetal pigment epithelial cell transplant in a patient with geographic atrophy, *Retina*, 19:540-5 (1999).
21. Valentino A, Kaplan H J, Del Priore L V. Retinal pigment epithelial repopulation in monkeys after submacular surgery, *Arch Ophthalmol*, 113:932-8 (1995).
22. Del Priore L V, Hornbeck R, Kaplan H J. Debridement of the pig retinal epithelium in vivo, *Arch Ophthalmol*, 113: 939-44 (1995).
23. Del Priore L V, Kaplan H J, Hornbeck R. Retinal pigment epithelial debridement as a model for the pathogenesis and treatment of macular degeneration, *Am J Ophthalmol*, 122: 629-43 (1996).
24. Leonard D S, Zhang X-G, Panozzo G, Sugino I K, Zarbin M A. Clinicopathologic correlation of localized retinal pigment epithelium Debridement, *Invest Ophthalmol Vis Sci.*, 38:1094-109 (1997).
25. Gouras P, Floord M T, Kjeldbye H, Bilek M K, Eggers H. Transplantation of cultured human retinal epithelium to Bruch's membrane of the owl monkey's eye, *Curr. Eye Res.*, 4:253-65 (1985).
26. Phillips S J, Sadda S, Liu H. Tso M O M, Binder S. Autologous transplantation of retinal pigment epithelium after mechanical debridement of Bruch's membrane, *Invest Ophthalmol Vis Sci.*, in press (2002).
27. Guymer R, Luthert P, Bird A. Changes in Bruch's membrane and related structures with age, *Prog. Retin. Eye Res.*, 18:59-90 (1998).
28. Grisanti S., et al. Immunity and Immune Privilege elicited by cultured retinal pigment epithelial cell transplants, *Invest Ophthalmol Vis Sci.*, 38:1619-26 (1997).
29. Gabrielan K., et al. Cellular response in rabbit eyes after human fetal RPE transplantation, *Graefes Arch Clin. Ophthalmol*, 237:326-35 (1999).
30. Yamamoto S., et al. Retinal Pigment Epithelial transplants and retinal function in RCS rats, *Invest Ophthalmol Vis Sci.*, 34:3068-75 (1993).
31. Pfefer B A. Improved methodology for cell culture of human and monkey retinal pigment epithelium, *Prog. Retin. Eye Res.*, 10:251-91 (1991).
32. Steinberg R H, Wood I. In: Zinn K M, Marmor M F, eds. The Retinal Pigment Epithelium, *Cambridge, Mass.: Harvard University Press*, 32-44, (1979).
33. Floord M T, Gouras P, Kjeldbye H. Growth characteristics and ultrastructure of human retinal pigment epithelium in vitro, *Invest Ophthalmol Vis Sci.*, 19:1309-20 (1980).
34. Hu J, Bok D. A cell culture medium that supports the differentiation of human retinal epithelium into functionally polarized monolayers, *Molecular Vision*, 7:14-9 (2000).
35. Flannery J G, Pfefer B A, Bok D. Transepithelial transport of vitamin A by monolayers of human RPE in vitro, *Invest Ophthalmol Vis Sci.*, 26:3 (1985).
36. Abi A, Binder S, Harrer E. Multifokale elektroretinographie (mERG) zur Verlaufskontrolle bei subretinaler Chirurgie mit autologer RPE-Transplantation bei Patienten mit AMD, *Spektrum Augenheilk*, 15:185-8 (2001).
37. Bilbao K V, Leng T, Fung A E, et al. A biodegradable matrix facilitates the use of lens capsule as a substrate for subretinal cell transplantation, *ARVO 2002, IOVS* 43/4, 3441.
38. Farrokh-Siar L, Kourous A, Rezai A, et al. Cryoprecipitate : An autologous substrate for human fetal retinal pigment epithelium, *Ex. Eye Research*, 19;2, 89-94, (1999).
39. Dutt K, et al. Extracellular matrix mediated growth and differentiation in human pigment epithelial cell line 0041, *Current Eye Research*, 10 (12): 1089-100 (1991).
40. LU L, Yaszemski M J, Mikos A G. Retinal pigment epithelium engineering using synthetic biodegradable polymers, *Biomaterials*, 22:3345-55 (2001).
41. Fung A E, Lee C J, Leng T, et al. Tissue engineered lens capsule as a substrate for IPE and RPE transplantation, *ARVO 2002, IOVS* 43/4, 3452.
42. Thuman G, Schaefer F, Finkham J, et al. Growth of Iris pigment epithelial cells on a biodegradable substratum, *ARVO 2002, IOVS* 43/4 3454.
43. Lappas A, Rezai K A, Bernd T, et al. Iris pigment epithelium transplantation-in vitro techniques Presented at the "International Conference of Subretinal Surgery and Retinal Transplantation," *Vienna* 1998.
44. Giordano G G, Thomson R C, Ishaug S L, et al. Retinal pigment epithelium cells cultured on synthetic biodegradable polymers, *J of Biomedical Material Research*, 34:87-93, (1997).
45. Korte G E, Reppucci V, Henkind P. RPE, Destruction causes choriocapillary atrophy, *Invest Ophthalmol Vis Sci.*, 25:1135-45 (1984).
46. Kuwabara T. Ishikawa Y, Kaiser-Kupfer M. Experimental model of gyrate atrophy in animals, *Ophthalnzology*, 88:3314 (1981).
47. Takeuchi M, Itagaki T, Takahashi K. Changes in the intermediate stage of retinal degeneration after intravenous 48. Koh S-W M. The chick retinal pigment epithelium grown on permeable support demonstrates function polarity, *Exp. Cell Res.*, 181:331-47 (1998).
49. Heth C A, Yankauckas M A, Adamian M, Edwards R B. Characterization of retinal pigment epithelial cells cultured on microporous filters, *Curr. Eye Res.*, 6:1007-19 (1987).
50. Albert D M, Tso M O M, Rabson A S. In vitro growth of pure culture of retinal epithelium, *Arch Ophthalmol*, 88:63-9 (1972).
51. Del Priore L V, Tezel T H. Reattachment rate of human retinal pigment epithelium to layers of human Bruch's membrane, *Arch Ophthalmol*, 116:335-41 (1998).
52. Tezel T H, Kaplan H J, Del Priore L V. Fate of human retinal pigment epithelial cells seeded onto layers of human Bruch's membrane, *Invest. Ophthalmol. Vis. Sci.*, 40:467-76 (1999).
53. Kim J C, Tseng S C G. Transplantation of preserved human amniotic membrane for surface reconstruction in severely damaged rabbit corneas, *Cornea*, 14:473-84 (1995).
54. Dua H S, Azuara-Blanco A. Amniotic membrane transplantation, *Br. J Ophthalnol*, 83:748-52 (1999).
55. Kruse F E, Voelcker H E, Rohrschneider K. Amniotic membrane transplantation (AMT) for ocular surface reconstruction, *Ophthalmology*, 122 (1998).
56. Sippel K C, Ma J J K, Foster C S. Amniotic membrane surgery, *Curr. Opin. Ophthalmol*, 12:269-81 (2001).
57. Tseng S C G, Tsubota K. In: Holland E J, Mannis M J, eds. Ocular Surface Diseases: Medical and Surgical Management. first ed., *Springer*, 226-31 (2001).
58. Kruse F E, Joussen A M, Rohrschneider K, You L, Sinn B, Baumann I, et al. Cryoperserved human amniotic membrane for ocular surface reconstruction, *Graefe's Arch. Clin. Exp. Ophthalmol*, 238:68-75 (2000).
59. Gelanze M, Breipohl W, Wiedemann P, Naib-majani W, Heimann K. First experimental iris pigment epithelial cell transplantation in subretinal space of RCS rats, *Invest Ophithalmol Vis Sci.*, 34:1097 (1993).
60. Gelanze M, Meneses P, Rosenfeld , Duvoisin R M, Coleman D J. Long-term results of autologous transplantation of iris pigmented epithelial cells into the subretinal space, *Invest Ophthalmol Vis. Sci.*, 38:334 (1997).
61. Lai W, Rezaei K A, Farrokh-Siar L, Pearlmann J, Shu J, Patel S C, et al. A new method of culturing and transferring iris pigment epithelium, *Invest Ophthalmol Vis Sci.*, 38:335 (1997).
62. Grueterich M, Espana E, Tseng S C G. Connexin 43 expression and proliferation of human limbal epithelium on intact and denuded amniotic membrane, *Invest Ophthalmol Vis. Sci.*, 43:63-71 (2002).
63. Meller D, Tseng S C G. Conjunctival epithelial cell differentiation on amniotic membrane, *Invest. Ophthalmol. Vis. Sci.*, 40:878-86 (1999).
64. Bhatt N S, Newsome D A, Fenech T, et al. Experimental transplantation of human retinal pigment epithelial cells on collagen substrates, *Am J Ophthalmol*, 117:214-21 (1994).
65. Del Priore L V, Tezel T H, Hornbeck R, et al. Transplantation of retinal pigment epithelial sheets into the subretinal space of porcine eye, *Invest Ophthalmol Vis. Sci.*, 38:1207 (1997).
66. Oganesian A, Gabrielian K, Verp M, et al Transplantation of human fetal retinal pigment epithelial as a three dimensional culture system, *Invest Ophthalmol Vis. Sci.*, 38:1568 (1997).
67. Rezai K A, Farrokh-Siar L, Godowski K, et al. Transplantation of human fetal retinal pigment epithelium spheroids, *Invest Ophthalmol Vis. Sci.*, 40:3137 (1999).
68. Hadlock T, Singh S, vacanti J P. Mclaughlin B J. Ocular cell monolayers cultured on biodegradable substrate, *Tissue Eng.*, 5:187-96 (1999).
69. Lu L, Garcia C A, Mikos A G. Retinal pigment epithelium cell culture on thin biodegradable poly(DL-lactic-co-glycolic acid) film, *J Biomater Sci. Polymer Edn.*, 9:1187-205 (1998).
70. Singh S, Woerly S, Mclaughlin B J. Natural and artificial substrates for retinal pigment epithelial monolayer transplantation, *Biomaterials*, 22:3337-43 (2001).
71. Kiilgaard J F, Nicolini J, Wiencke A K, et al. Growth of porcine RPE cells on extracellular matrix and on porcine anterior capsule, *Invest Ophthalmol. Vis. Sci.*, 39:100 (1998).

EQUIVALENTS

While this invention has been particularly shown and described with references to preferred embodiments thereof, it will be understood by those skilled in the art that various changes in form and details may be made therein without departing from the scope of the invention. Those skilled in the art will recognize, or be able to ascertain using no more than routine experimentation, many equivalents to the specific embodiments described herein. Such equivalents are intended to be encompassed in the scope of the following claims.

What is claimed is:

1. A method for treating a retinal disease, comprising inserting in a subretinal space of a human patient in need thereof a composite comprising amniotic membrane and non-immortalized human retinal pigment epithelial cells or non-immortalized human retinal pigment epithelial equivalent cells on the membrane, wherein the number of non-immortalized human retinal pigment epithelial cells or non-immortalized human retinal pigment epithelial equivalent cells on the membrane is from about 16,000 to about 20,000 per 4 $mm^2$ of amniotic membrane.

2. The method of claim 1, wherein the retinal disease that is treated is selected from the group consisting of retinal detachment, gyrate atrophy, choroideremia, and age-related macular degeneration.

3. The method of claim 1, wherein the amniotic membrane is human amniotic membrane.

4. The method of claim 1, wherein the retinal pigment epithelial cells comprise retinal pigment epithelial cells cultured on the amniotic membrane.

5. The method of claim 1, wherein the composite further comprises a pharmaceutically active molecule.

6. The method of claim 5, wherein the pharmaceutically active molecule is selected from the group consisting of growth factors, enzymes, and therapeutic drugs.

7. The method of claim 1, wherein the amniotic membrane is epithelially denuded.

8. The method of claim 1, wherein the amniotic membrane is intact amniotic membrane comprising a basement membrane and a stroma.

9. The method of claim 8, wherein mesenchymal cells are added to at least one side of the stroma before insertion in a subretinal space of a patient.

10. The method of claim 9, wherein the mesenchymal cells are fibroblasts.

11. The method of claim 1, wherein the amniotic membrane is treated on at least one side with excimer laser ablation before insertion in a subretinal space of a patient.

12. The method of claim 11, wherein the excimer laser ablation alters the thickness of the stromal side or basement membrane side of the amniotic membrane.

13. The method of claim 1, wherein the retinal pigment epithelial equivalent cells comprise cells selected from the group consisting of iris pigment epithelial cells, retinal pigment epithelial cells differentiated from at least one adult or embryonal stem cell, cells derived from neural retinal cells, and cells derived from a ciliary body.

14. The method of claim 6, wherein the pharmaceutically active molecule is a growth factor selected form the group consisting of retinal pigment epithelium-derived growth factor, transforming growth factor-beta, and interleukin-10.

15. The method of claim 1 wherein the composite is formed by:
(a) applying at least one retinal pigment epithelial cell or retinal pigment epithelial equivalent cell to an amniotic membrane; and
(b) culturing the retinal pigment epithelial cell or retinal pigment epithelial equivalent cell on the membrane under conditions suitable for growth for a period of time sufficient to produce a plurality of cultured cells.

* * * * *